United States Patent [19]
Mandal et al.

[11] Patent Number: 5,840,998
[45] Date of Patent: Nov. 24, 1998

[54] SIDE CHAIN CHLORINATION OF AROMATIC AND HETEROCYCLIC ETHERS

[75] Inventors: Sanjay Mandal, Grand Island; Kevin R. Benson, West Seneca; George Piotrowski, Cheektowaga, all of N.Y.

[73] Assignee: Occidental Chemical Corporation, Niagra Falls, N.Y.

[21] Appl. No.: 46,525

[22] Filed: Mar. 24, 1998

[51] Int. Cl.$^6$ .................................................. C07C 43/225
[52] U.S. Cl. ............................................................ 568/655
[58] Field of Search ............................................. 568/655

[56] References Cited

U.S. PATENT DOCUMENTS 5,440,051  8/1995  Marhold .
5,484,932  1/1996  Marhold .

OTHER PUBLICATIONS

An Article by F. Kurzer et al. "P–Tolvenesulfenylchloride" in Organic Synthesis, vol. 4, p. 934 (1967).

Primary Examiner—Johann Richter
Assistant Examiner—Taofiq A. Solola
Attorney, Agent, or Firm—Richard D. Fuerle

[57] ABSTRACT

Disclosed is a method of chlorinating a side chain of a aromatic or heterocyclic ether. The aromatic or heterocyclic ether is mixed with a fluorine-containing aliphatic solvent. The aromatic or heterocyclic ether is contacted with chlorine radical at an elevated temperature which results in its chlorination. The chlorinated product is preferably insoluble in the solvent and separates, forming two phases. The solvent phase can be recycled and reused.

21 Claims, No Drawings

SIDE CHAIN CHLORINATION OF AROMATIC AND HETEROCYCLIC ETHERS

BACKGROUND OF THE INVENTION

This invention relates to a method of chlorinating the side chains of aromatic and heterocyclic ethers. In particular, it relates to performing such chlorinations in aliphatic fluorinated solvents.

Until recently, aryl ethers were chlorinated in carbon tetrachloride. However, carbon tetrachloride is now considered to be environmentally deleterious and its use as a solvent for this type of reaction is no longer permitted. Thus, a search has been conducted by the chemical industry to find other acceptable solvents for this reaction. For example, U.S. Pat. Nos. 5,440,051 and 5,484,932 disclose performing these chlorination reactions in certain aromatic solvents. The substrate—the compound to be chlorinated—is dissolved in the aromatic solvent for the chlorination reaction. After the chlorination is complete, the product, which is also soluble in the solvent, is separated from the solvent by distillation.

SUMMARY OF THE INVENTION

We have discovered that side chains on aromatic and heterocyclic ethers can be chlorinated in aliphatic fluorinated solvents. We have further discovered that these solvents offer a number of advantages over aromatic solvents, such as those described in the prior art. For example, for many substrates and fluorinated solvents, the product is insoluble in the solvent so that two phases form—a product phase and a solvent phase. Thus, the product is easily separated from the solvent and distillation to separate the product from the solvent is eliminated. Because two phases are formed, the solvent can be easily recycled and reused and the process can be run continuously. Many of the fluorinated solvents of this invention are unreactive, non-toxic, environmentally acceptable, and non-flammable.

DESCRIPTION OF THE PREFERRED EMBODIMENTS

Substrate

The process of this invention can be applied to chlorinate a methyl or ethyl hydrogen on a side chain of a aromatic or heterocyclic ether (α-chlorination). In particular, the substrate has the formula ROR', where R is methyl or ethyl, R' is a group containing an aromatic ring or a heterocyclic ring, and the RO group is bonded directly to that aromatic or heterocyclic ring. The R' group preferably contains an aromatic ring as those substrates are commercially more important. Examples of aromatic rings include benzene, naphthalene, and anthracene. A single benzene ring is preferred, and the most preferred substrates are methoxybenzenes, such as anisole or a substituted anisole, which have the formula:

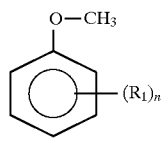

where each $R_1$ is independently selected from $NO_2$, X, $CX_3$, or $OCX_3$, where each X is independently selected from halogen and n is an integer from 0 to 3. If n is 1, R is preferably chlorine and is preferably in the para position as those substrates are more important commercially than other substituted methoxybenzenes. Examples of substituted methoxybenzenes include 4-chloroanisole (4-chloromethoxybenzene), 2-, 3-, or 4-fluoroanisole, 3-(trifluoromethyl) anisole, and 3-methoxy-5-(trifluoromethyl) aniline. However, the preferred substrate is anisole (n=0) because the chlorination product, α,α,α-trichloromethoxybenzene (TCMB), is a commercially important product.

Heterocyclic rings can have 5 or 6 atoms in the ring and the hetero atom (or atoms) can be nitrogen, sulfur, or oxygen. Examples of substrates containing a heterocyclic ring include 2-methoxypyridine, 4-methoxypyridine, 2-methoxypyrazine, 4-methoxypyrazine, 2-methoxythiophene, and 4-methoxythiophene.

Fluorinated Solvent

The fluorine-containing solvents useful in this invention are aliphatic compounds (i.e., they do not contain an aromatic ring) that boil between 50° and 110° C. The solvents are either liquid at room temperature or are liquid at the reaction temperature; preferably, they are liquid at room temperature as those solvents are easier to use. Preferably, the product of the reaction is immiscible with or insoluble in the solvent, so that the product can be easily separated from the solvent without using distillation. The solvent must be unreactive with the substrate and with the chlorine radical. Examples of suitable solvents include fluorocarbons (i.e., perfluorocarbons and hydrofluorocarbons), perfluorocycloalkanes, perfluorinated nitrogen-containing ring compounds, and fluoroethers.

Examples of fluorocarbons include compounds having the general formula $C_mH_nF_{2m+2-n}$, where m is 6 to 10, and n is 0 to m/2 if m is even and 0 to (m+1)/2 if m is odd. Perfluorocarbons (i.e., n=0) are preferred over hydrofluorocarbons (i.e., n≧1) because they are immiscible with product, which facilitates separation after chlorination. Examples of suitable perfluorocarbons include perfluorohexanes, and perfluoroheptanes. The preferred perfluorocarbon is perfluorohexane because its boiling point is low and ring chlorination is minimized when the reaction is performed at reflux and the reflux temperature is low (i.e., below 60° C.). Examples of suitable hydrofluorocarbons include 2,3-dihydrodecafluoropentane (DHDFP), 1-hydrotridecafluorohexane, and nonafluoro-hex-1-ene. The preferred hydrofluorocarbon is DHDFP because it is commercially available.

Perfluorocycloalkanes are ring compounds containing only carbon and fluorine. Examples include perfluorocyclohexane, perfluoromethylcyclohexane, perfluoro-1,2-dimethylcyclohexane, perfluoro-1,3-dimethylcyclohexane, perfluorocycloheptane, and perfluorocyclooctane. The preferred perfluorocycloalkane is perfluorocyclooctane because its boiling point allows operation at reflux with minimum loss through the condenser.

Perfluorinated nitrogen-containing ring compounds are ring compounds having a nitrogen in the ring, where all the single bonds are to fluorine. Examples of perfluorinated nitrogen-containing ring compounds include perfluoro(4-methyl morpholine), $C_5F_{11}NO$, which has the structure:

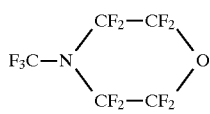

and perfluoro(N-methyl piperidine), $C_6F_{13}N$, which has the structure:

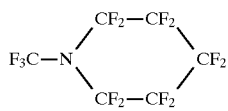

Both compounds are commercially available.

Linear fluoroethers include compounds having the general formula $F_{2p+1-q}H_qC_p$—O—$C_rH_sF_{2r+1-s}$, where p and r are each independently selected from integers from 3 to 6, q is an integer from 0 to 2p, and s is an integer from 0 to 2r+1. Examples of suitable linear perfluoroethers (i.e., q=0 and s=0) include bis(perfluoropropyl)ether, bis(perfluorobutyl)ether, and bis(perfluoropentyl)ether. The preferred perfluoroether is bis(perfluorobutyl)ether because its boiling point allows operation at reflux with minimum loss through the condenser. Examples of alkyl perfluoroethers (i.e., q=0 and s=2r+1) include (perfluoroisopropyl)ethyl ether, (perfluoroisopropyl)methyl ether, (perfluorobutyl) methyl ether, and (perfluorobutyl)ethyl ether. (Perfluoro) isopropylethyl ether is preferred because its vapor pressure is close to the vapor pressure of BTF. Cyclic perfluoroethers, such as

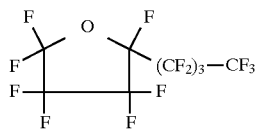

sold by ACROS as "FC-75" solvent and perfluoropolyethers, such as

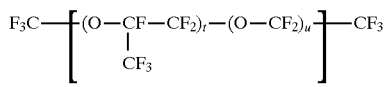

where t is between 1 and 8 and u is between 1 and 20 (sold as "Fomblin" solvent by Ausimont), can also be used.

The preferred fluorinated solvent is perfluorohexane because perfluorohexane contains few other isomers and therefore isomer peaks do not show when the reaction is followed by gas chromatography (GC). The amount of fluorinated solvent should be about 10 to about 90 wt %, based on the weight of the composition. If less fluorinated solvent is used, ring chlorination may increase and more solvent is unnecessary and is a waste of reactor volume. Preferably, about 40 to about 70 wt % fluorinated solvent is used.

Chlorine Radical

The substrate is chlorinated with gaseous chlorine that has been split into the chlorine radical Cl·. Any source of chlorine radicals can be used in this reaction. While UV light is preferred for generating chlorine radicals, a free-radical initiator can be used instead. Examples of suitable free-radical initiators include azo compounds such as 1,1'-azobis (isobutyronitrile) (AIBN) and 1,1'-azobis(cyclohexane carbonitrile), $NCC_6H_{10}N=NC_6H_{10}CN$, sold by Dupont as "VAZO," and peroxides such as benzoyl peroxide, diacetyl peroxide, and succinyl peroxide. The preferred free-radical initiator is VAZO because of its long half life at 88° C. (10 hours). If a free-radical initiator is used, the amount should be about 0.01 to about 10 wt %, based on the weight of substrate. If less free-radical initiator is used, the reaction is too slow and more initiator is unnecessary. Preferably, the amount of free-radical initiator is about 0.1 to about 1.0 wt %.

Chlorination Reaction

The chlorination reaction is performed by heating the mixture of the reactants until the product forms. The reaction temperature will depend upon the particular substrate used. For example, anisole is preferably heated at a temperature of about 60° to about 120° C. We have discovered that it is preferable to keep the reaction temperature at reflux as that seems to result in the production of less chloro-phenol by-products. We have also found that it is preferable to meter into the solvent stoichiometric quantities of the substrate and the chlorine as this seems to result in less ring chlorination. Also, it is preferable to perform the reaction continuously as this is more efficient and less costly. The end of the reaction can be determined by gas chromatography (GC).

The chlorinated product is generally a liquid which, if a preferred solvent is used, will be insoluble in the solvent, resulting in the formation of two phases, a product phase and a solvent phase. The two phases can be easily separated by, for example, decantation, thereby eliminating a distillation step. The solvent can be recycled as the product is removed.

The following examples further illustrates this invention.

EXAMPLE 1

Into a 250 mL photochlorination apparatus equipped with a 100 W medium pressure Hanovia UV light (air cooled), a reflux condenser, an inlet for the addition of anisole, a thermocouple, and an inlet for chlorine was placed 500 g of "FC-75" solvent. The reactor was heated to reflux (102° C.), by means of a thermal tape around the apparatus and a light. Both chlorine and anisole were metered into the reactor at the same time. The chlorine was added at a rate of 243 mL/min for half an hour, and then at 164 mL/min for the remainder of the reaction. The anisole (35 g, 7 wt %, based on the weight of the solvent) was added at a rate of 30 g/hr using an FMI pump. Both anisole and the product of the reaction were immiscible with the solvent. The product was the top layer of the two layers in the reactor. An assay of the top layer by GC showed a 92.3% yield of the desired TCMB.

EXAMPLE 2

Example 1 was repeated with similar results using 392 g of perfluorohexane, $C_6F_{14}$, sold by ACROS as "FC-72" solvent. The reactor was heated to reflux (55° C.). The chlorine was added at a rate of 200 mL/min for an hour, and then at 100 mL/min for the remainder of the reaction. The anisole (69.2 g, 17.65 wt %, based on the weight of the solvent) was added at a rate of 30 g/hr. The yield of TCMB was 93.5%.

EXAMPLE 3

Example 1 was repeated with similar results using 496.6 g of "Fomblin" solvent. The reactor was heated to reflux (109° C.). The chlorine was added at a rate of 200 mL/min for three hours, and then at 100 mL/min for the remainder of the reaction. The anisole (88.4 g, 17.8 wt %, based on the weight of the solvent) was added at a rate of 30 g/hr. The yield of TCMB was 89.8%.

EXAMPLE 4

Example 1 was repeated with similar results using 377 g of hydrofluoroether, $C_5H_3F_9O$, sold by 3M as "HFC-7100" solvent. The reactor was heated to reflux (60° C.). The chlorine was added at a rate of 243 mL/min for four hours. The anisole (55 g, 14.6% by weight of the solvent) was added at a rate of 30 g/hr. The yield of TCMB was 93.9%.

We claim:

1. A method of chlorinating a side chain of an aromatic or heterocyclic ether comprising
   (A) preparing a mixture of a fluorine-containing aliphatic solvent and an aromatic or heterocyclic ether having a chlorinatable side chain; and
   (B) contacting said aromatic or heterocyclic ether in said solution with chlorine radical at an elevated temperature.

2. A method according to claim 1 wherein said aromatic or heterocyclic ether has the general formula ROR', where R is methyl or ethyl, R' is a group containing at least one aromatic or heterocyclic ring, and said RO group is bonded directly to said aromatic or heterocyclic ring.

3. A method according to claim 2 wherein said RO group is bonded directly to an aromatic ring.

4. A method according to claim 3 wherein said aromatic or heterocyclic ether is a methoxybenzene.

5. A method according to claim 4 wherein said aromatic or heterocyclic ether is anisole.

6. A method according to claim 5 wherein said elevated temperature is about 60° to about 120° C.

7. A method according to claim 1 wherein the product of said chlorination is insoluble in said solvent.

8. A method according to claim 6 wherein said solvent is recycled.

9. A method according to claim 1 wherein said aromatic or heterocyclic ether and chlorine gas are metered into said solvent in about a stoichiometric proportion.

10. A method according to claim 1 performed continuously.

11. A method of making a trichloromethoxybenzene by chlorinating a methoxybenzene comprising
    (A) preparing a mixture of said methoxybenzene and about 10 to about 90 wt % of a solvent selected from the group consisting of perfluorocarbons, hydrofluorocarbons, perfluorocycloalkanes, perfluorinated nitrogen-containing ring compounds, and fluoroethers;
    (B) contacting said methoxybenzene with chlorine gas at reflux;
    (C) exposing said chlorine gas to ultraviolet light, whereby chlorine radical is formed, α-chlorinating said methoxybenzene to form said trichloromethoxybenzene, which is insoluble in said solvent;
    (D) separating said trichloromethoxybenzene from said solvent; and
    (E) recycling said solvent to step (A).

12. A method according to claim 10 wherein said methoxybenzene is anisole.

13. A method according to claim 11 wherein said elevated temperature is about 60° to about 120° C.

14. A method according to claim 10 wherein said methoxybenzene has the general formula

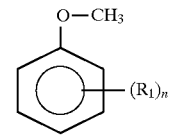

where $R_1$ is $NO_2$, X, $CX_3$, or $OCX_3$, where each X is independently selected from halogen and n is 1 to 3.

15. A method according to claim 10 wherein said methoxybenzene and said chlorine gas are metered into said solvent in about a stoichiometric proportion.

16. A method according to claim 10 wherein said solvent has the general formula $C_mH_nF_{2m+2-n}$, where m is 4 to 8 and n is 0 to m/2 if m is even and 0 to (m+1)/2 if m is odd.

17. A method according to claim 10 wherein said solvent is $C_5F_{11}NO$.

18. A method according to claim 10 wherein said solvent is a linear fluoroether having the general formula $F_{2p+1-q}H_qC_p$—O—$C_rH_sF_{2q+1-s}$, where p and r are each independently selected from integers from 3 to 6, q is an integer from 0 to 2p, and s is an integer from 0 to 2r+1.

19. A method according to claim 10 wherein s is 2r+1.

20. A method according to claim 10 wherein said solvent is a perfluoropolyether having the general formula

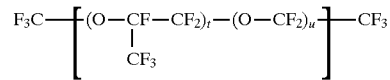

where t is 1 to 8 and u is 1 to 20.

21. A method of making trichloromethoxybenzene comprising
    (A) continuously metering anisole and chlorine gas in approximately a stoichiometric proportion into about 40 to about 70 wt % perfluorohexane heated to reflux;
    (B) continuously exposing said solvent to ultraviolet light, whereby chlorine radicals are formed which react with said anisole to form said trichloromethoxybenzene, which is insoluble in said perfluorohexane and separates from said perfluorohexane;
    (C) separating said perfluorohexane from said trichloromethoxybenzene; and
    (D) recycling said perfluorohexane to step (A).

* * * * *